United States Patent

Husson et al.

[11] Patent Number: 6,165,218
[45] Date of Patent: Dec. 26, 2000

[54] INTERVERTEBRAL PROSTHESIS

[75] Inventors: Jean-Louis Husson, Rennes, France; Walter Baumgartner, Winterthur; Stefan Freudiger, Bremgarten, both of Switzerland

[73] Assignee: Sulzer Orthopaedie AG, Baar, Switzerland

[21] Appl. No.: 09/249,934

[22] Filed: Feb. 12, 1999

Related U.S. Application Data

[62] Division of application No. 08/723,146, Sep. 30, 1996, Pat. No. 5,919,235.

[30] Foreign Application Priority Data

Nov. 8, 1995 [EP] European Pat. Off. .............. 95810701

[51] Int. Cl.$^7$ ....................................................... A61F 2/44
[52] U.S. Cl. .............................................................. 623/17
[58] Field of Search .................................. 623/17; 606/61

[56] References Cited

U.S. PATENT DOCUMENTS 5,171,280  12/1992  Baumgartner .............................. 623/17
5,350,397   9/1994  Palermo ..................................... 623/17

Primary Examiner—Michael J. Milano
Attorney, Agent, or Firm—Townsend and Townsend and Crew LLP

[57] ABSTRACT

An implant, in particular an intervertebral prosthesis, which consists of an elongated elastic body which is form-elastic and takes on the form of a spiral S in the force free state. The spiral can be drawn by a reverse winding up into an insertion instrument which is only insubstantially larger in the insertion region than the cross-section of the elongated elastic body in order to reach the inner space of an intervertebral disc through a small opening in the annulus fibrosus and to push in and sever off the self winding spiral when the interior is filled. This has the advantage that inner spaces of differing sizes can be filled with the same spiral.

1 Claim, 3 Drawing Sheets

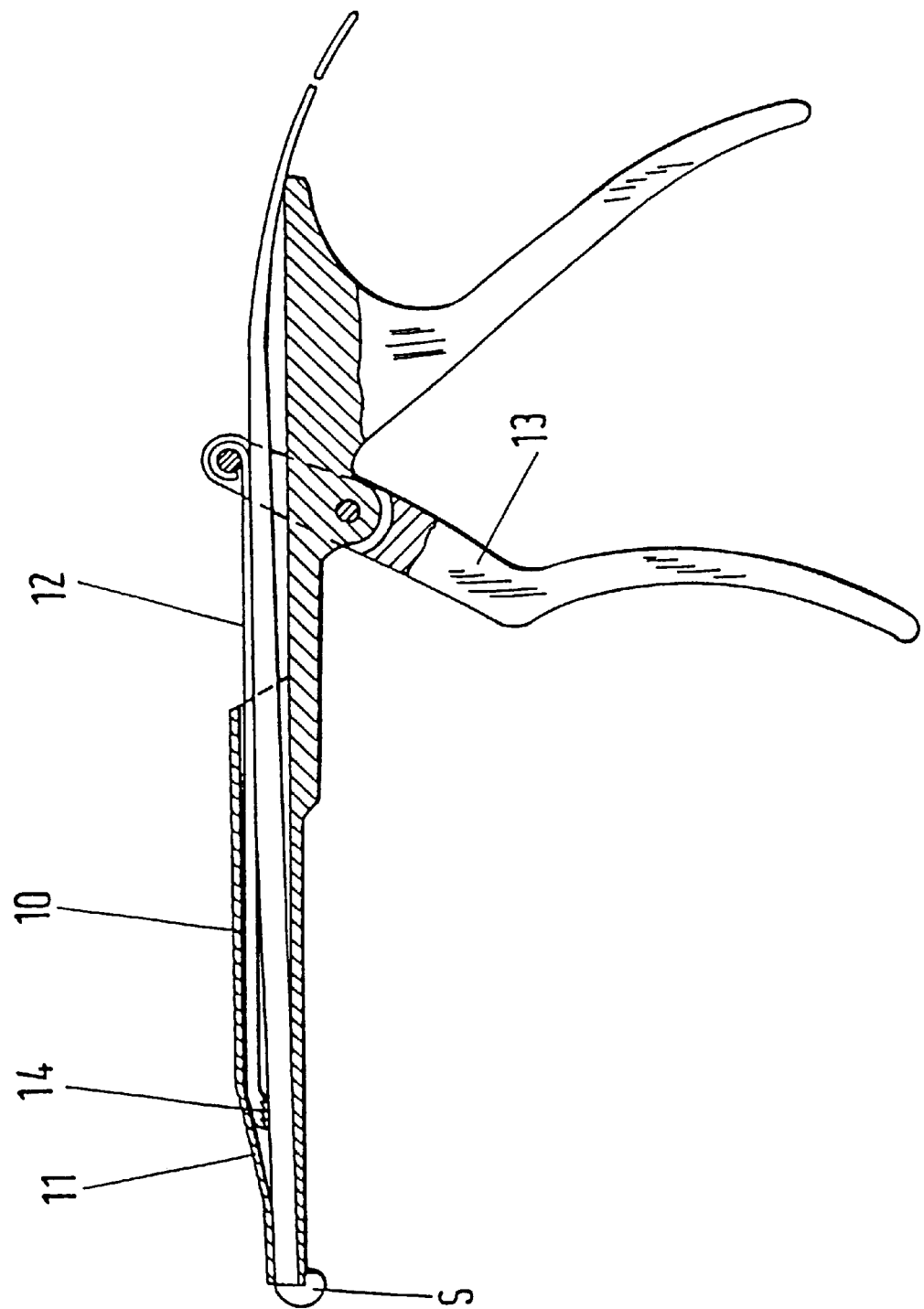

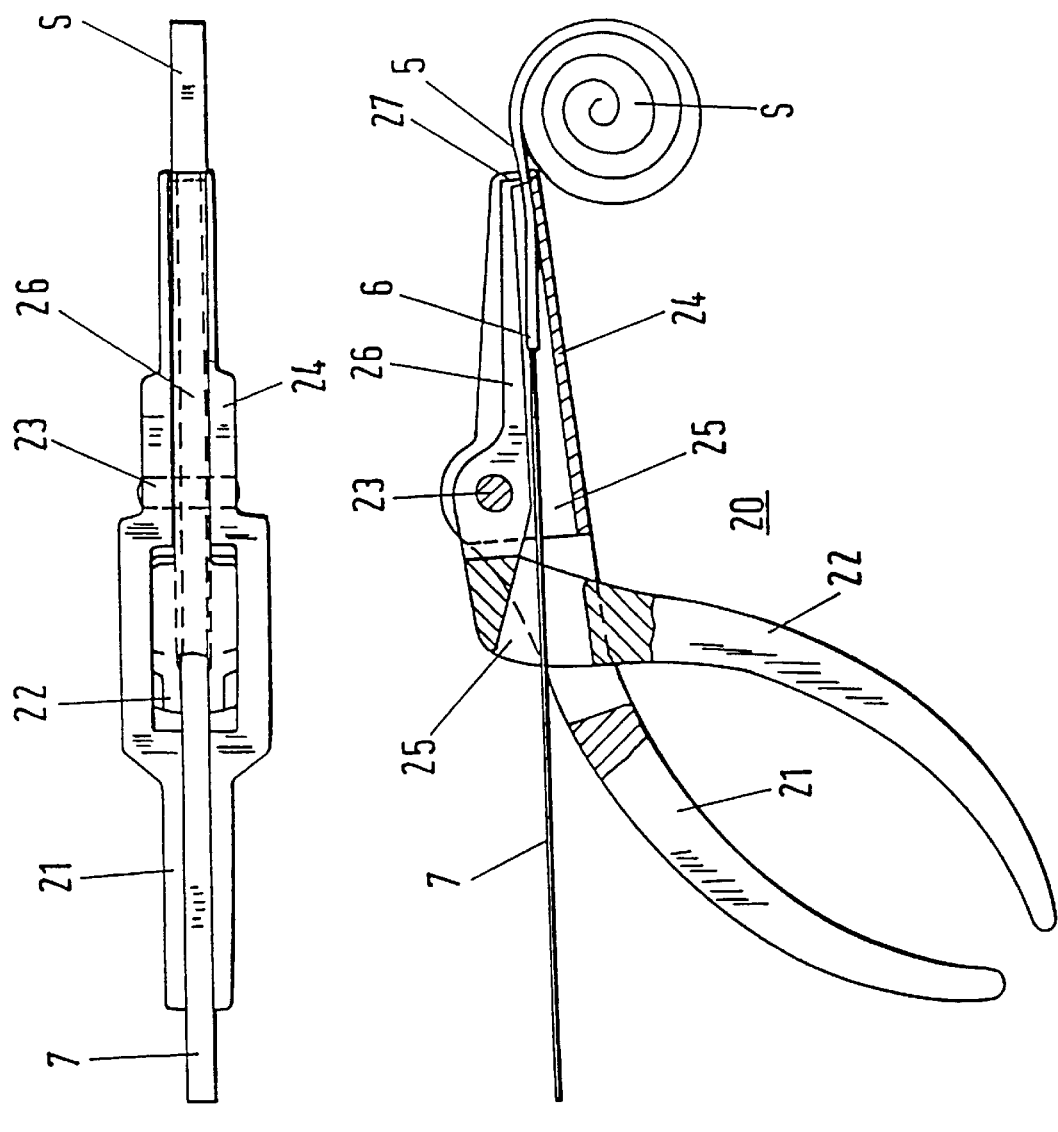

INTERVERTEBRAL PROSTHESIS

This application is a division of application Ser. No. 08/723,146, filed Sep. 30, 1996, now U.S. Pat. No. 5,919,235.

BACKGROUND OF THE INVENTION

1. Field of the Invention

The invention relates to an implant, in particular an intervertebral prosthesis, consisting of an elongated elastic body.

2. Description of the Prior Art

A prosthesis of this type is known from EP-A-0 453 393. It serves as replacement for a damaged intervertebral disc nucleus (nucleus pulposus). With this prosthesis the outer ring (annulus fibrosus) of a natural intervertebral disc remains intact for the most part. The known prosthesis consists of a fluid-tight hollow body which is filled with an incompressible flowable medium. This prosthesis requires for its implantation a specially formed insertion instrument by means of which the hollow body is intraoperatively coiled up into a spiral form and can subsequently be filled. This places high demands on the skill of the surgeon on the one hand, as well as on the manufacture of the insertion instrument with respect to the coiling mechanism, as well as with regard to the filling apparatus. Furthermore, the leak-proofing criteria of the hollow body represent a long-term risk when the great stresses in the region of the vertebral column are taken into account. After the body has been rolled up in the intervertebral region and filled, the free end lies in contact with the annulus fibrosus, if the tool which acts at the center of the spiral for filling and sealing is removable without producing cavities. Only if no migration of spiral elements into other cavities can occur can the radially directed forces arising under the stress be compensated for and the spiral achieve the desired support function.

SUMMARY OF THE INVENTION

The object of the invention is to provide an implant which permits a simple handling.

This object is satisfied by an implant in accordance with the present invention, which comprises an elongated elastic body which is form-elastic and takes on the form of a spiral in a force free state. The cross-section of the body is preferably rectangular, and the edges can also be rounded off. It is also possible to use bodies with a roundish cross-section as long as an essentially form-fitted, tilt-proof position of the spiral is retained under load. The cross-section of the elastic body need not be constant over its entire length, but rather it turns out that its thickness can preferably decrease in the outward direction. Such a spiral has the advantage that it winds itself, does not bend when thrust in and can be severed at a suitable rolled-up length.

The implant as such can take the form of a cylindrical disc, i.e. can be made flat, or else can have inward and/or outward curvatures which follow the contours of the vertebral surfaces. In this way, the forces produced under load can be more uniformly distributed over the vertebral surfaces. The diameter of the spiral is preferably chosen such that the space within the annulus fibrosus is filled out.

In order to insert the intervertebral disc, it has proved advantageous to attach a stiffening means in the form of a plastic or metal band at the free end of the spiral via which a severing device can be guided up to a desired point of severance. The band preferably has no curvature in the force free state. After a successful implantation the band is severed off from the implanted spiral along with that portion of the spiral not required by means of the severing device.

In order to be able to check the location of the implant intraoperatively and postoperatively, it is recommendable to provide X-ray-positive markings in the form of spheres or of a thread on or along the inside of the elastic body.

The material of which the elastic body is manufactured should correspond essentially to the elastic properties of an intervertebral disc so that the forces arising are as far as possible transmitted uniformly to the vertebral surface. The use of polyurethane or polyurethane-silicon mixtures, which have a Shore hardness of approximately 80A, has proved advantageous. Foams of the most diverse plastics can also be used as long as they satisfy the elastic requirements.

In an especially preferred embodiment, the spiral has a central middle part about which the further turns wrap themselves closely. Only small intervening spaces arise, which fill up with intervertebral fluid in the implanted state where present and which do not permit a canting of the elastic body under radial forces. By means of a suitable height to width relationship a canting of the elastic body is prevented in general. The middle piece can basically have the form of a circular cylinder, but forms such as a sphere or ellipsoid have also proved useful. It is advantageous that a short, thin transition part be joined thereto via which the connection to the remaining spiral is established. This has the advantage that the spiral remains in the tightest surface—surface packing and the greatest possible area distribution is achieved while eliminating force peaks. In a simpler embodiment of the implant the central middle piece can also be dispensed with since the contribution of its area is small in comparison with the total area.

The height of the spiral corresponds essentially to the physiological intervertebral spacing. The preferred thickness with which the elastic body is to be executed results from the elastic properties of the material used. At the periphery of the spiral, after about three to five turns, depending on the material and the breadth of the turn, the thickness of the body can decrease since the applied forces should be primarily taken up centrally and since on the other hand the body should be capable of being severed at a corresponding position. In a further embodiment of the invention it is possible to adapt the height of the implant to the individual intervertebral spacings.

The severance should preferably take place inside the cavity, for which purpose the corresponding forces must be supplied by means of an instrument to be described in further detail.

The invention also relates to a process for manufacturing an intervertebral implant in the form of a spiral. For this purpose, the implant can in the simplest case, be cut out e.g. of a material plate of the corresponding thickness. Conventional saws, cutting wires or similar tools can be used as the cutting means. Lasers which are suitable for cutting plastics can, however, also be used. In particular, lasers such as the excimer lasers, which permit athermal cutting, are advantageous here, since they avoid for the most part the production of toxic by-products. An especially preferred process is the injection molding process, with the injection into the snail-shaped mold preferably taking place at the interior of the spiral. The implant thus obtained has a spiral form with tightly form-fitted turns.

The invention relates further to an apparatus for inserting the implant, which essentially has a tube with a rectangular cross-section into which the elastic body can be drawn in, and preferably so far that the middle piece just protrudes from the distal end of the tube. The cross-section of the tube corresponds essentially to the cross-section of the elastic body. The feeding of the body can be done by hand. However, feeding means in the form of a pusher tool which can be activated, e.g. via a lever mechanism, are preferably provided, together with a corresponding cross-sectional enlargement of the tube. The pusher tool has means at its distal end, standing in operative contact with the elastic body or the stiffening, which facilitate the feeding of the body. The means can consist of a roughening of the surface, or else of tooth-like projections with preferential orientation in the distal direction. This achieves a situation in which the extensions grip into the elastic body or the stiffening on advance of the pusher tool and push the latter along with the pusher tool, whereas they slide backwards over the surface on retraction of the pusher tool. A controlled feeding of the elastic body is thereby made possible. It is of additional advantage to provide the tube at its distal end with a one-sided narrowing of its cross-section which at its narrow end is just capable of taking up the elastic body only. This has the effect that the pusher tool, when pushed forwards, is simultaneously pushed downwards, and thus the force transmitting contact between the pusher tool and the body is increased.

The tube of the insertion apparatus can advantageously be curved as well, since the insertion of an implant into the intervertebral space is preferably done from the side dorsally. The curvature can be executed either upwards or downwards, or if desired, to the left or the right, depending on at which side the access is desired to occur. Here the insertion apparatus can also run out at the forward end in a wedge in order to adequately space neighboring vertebral bodies which have lost their separation by means of the wedge-formed part.

The invention relates further to an apparatus for cutting off the end of the spiral which is not required. After the intervertebral prosthesis has been implanted, the insertion apparatus is pulled back along the stiffening, which at least partially remains outside of the intervertebral region, and the cut-off instrument is pushed onto it. This instrument preferably has an action mechanism similar to a pair of pliers, and comprises two grip parts standing in contact with one another via a hinge. One jaw of the cutting part is executed to be hollow so that it can receive the stiffening. The other jaw has a cutting edge standing essentially transversely to the longitudinal axis of the pliers. The length of the jaws as well as the placement of the cutting edge in the distal direction are preferably chosen in such a manner that, on the one hand, a cut in the intervertebral region is possible, and on the other hand, that the required severance forces can be safely exerted. Here the elastic body is enclosed in such a manner that no foreign tissue parts are cut when the end of the spiral not required is cut off. Of course pliers whose grip parts stand at an angle to the longitudinal axis can also be used in accordance with the invention.

In an especially preferred embodiment, the insertion apparatus can also contain a cutting instrument. This can be realized for example, by providing a further pusher tool with a cutting blade at its distal end which extends perpendicular to the longitudinal axis of the apparatus. The cutting action is produced by the distal narrowing of the tube cross-section, in a manner similar to the feeding situation.

The implant has the advantage of being as simple as possible in its construction and of ensuring a supporting effect uniformly over a greater part of its area. The implant has the further advantage of not having to be fixed in a spiral form by additional means, but can be inserted with comparatively simple and easy to use instruments.

The invention relates further to a process for inserting a spiral implant into a cavity as can be used for the purposes of teaching, practice and demonstration.

BRIEF DESCRIPTION OF THE DRAWINGS

FIG. 3 is a schematic representation of an insertion apparatus;

FIG. 4 is a schematic representation of a severing apparatus, and

FIG. 5 is a schematic plan view of the severing apparatus of FIG. 4.

DETAILED DESCRIPTION OF THE PREFERRED EXEMPLARY EMBODIMENTS

The Figures deal with an implant, in particular an intervertebral prosthesis preferably of an elongated elastic body, which is form-elastic and takes on the form of a spiral S in the force free state. The spiral can be drawn by reverse winding up into an insertion instrument, which is only insubstantially larger in the insertion region than the cross-section of the elongated elastic body in order to reach the inner space of an intervertebral disc through a small opening in the annulus fibrosus and to push in and separate off the self winding spiral when the inner space is filled. This has the advantage that inner spaces of differing sizes can be filled with the same spiral.

Figure 1:
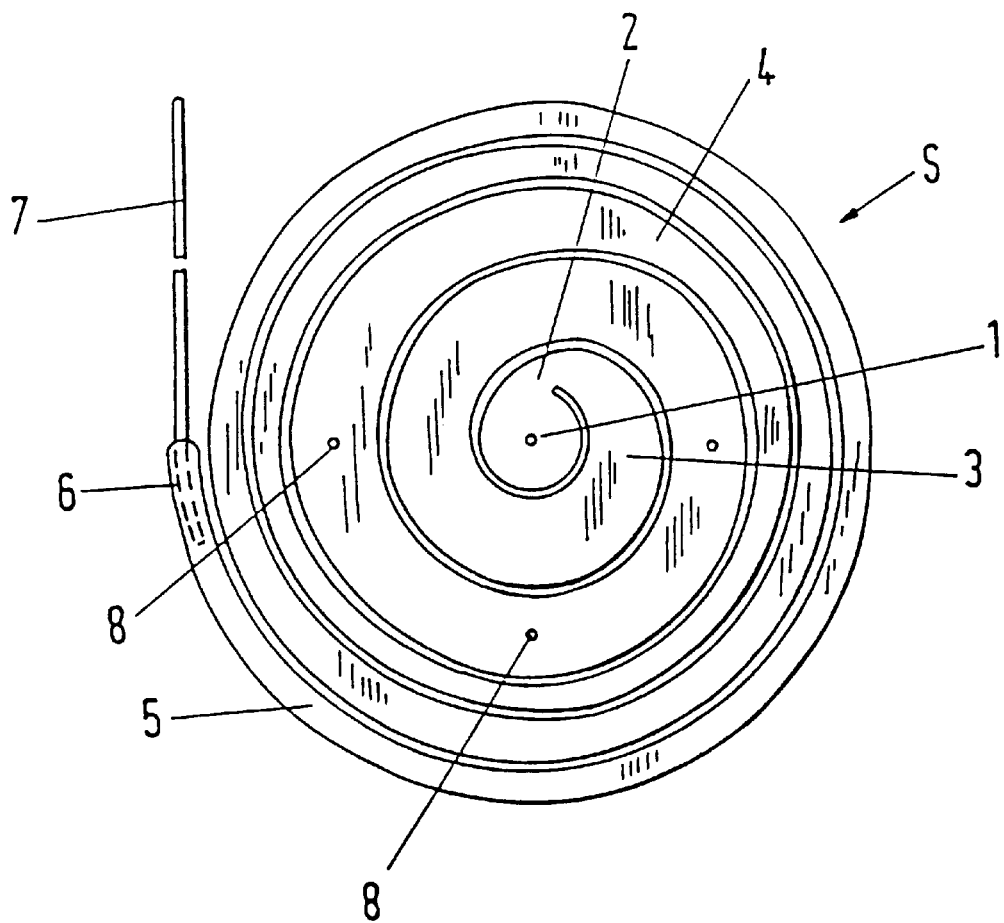
FIG. 1 is schematically and greatly enlarged the elastic body in the form of a spiral.

FIG. 1 shows the spiral implant with a central middle part 1, which has essentially the form of a cylinder. This is joined at the side by a thin region 2 which permits a pronounced angular deflection and thus a form-fitted transition to the spiral turn 3 connected to it, essentially without intervening spaces.

In the case that the middle piece is absent it is recommendable to execute the inner end of the spiral turn in such a manner that no tension peaks can occur under stress. This can be achieved, for example, by means of a rounded-off end.

The spiral turns connected to the transition region are form-fitted and have a constant breadth in the region of 2 to 5 mm so that canting under the loads to be expected can be excluded to the greatest extent. The implant comprises preferably 2–4 turns which are proof against canting. This is followed by a transition region 4 in which the breadth of the elastic body is reduced to such an extent that easy separation is possible, e.g. in about the region 5 of FIG. 1. The spiral is adjusted intra-operatively to the desired size through the number of turns. The support effect in respect to tilting is reduced per se in the outer turns, however it is sufficiently great in connection with the more form-stable inner turns.

Figure 2:
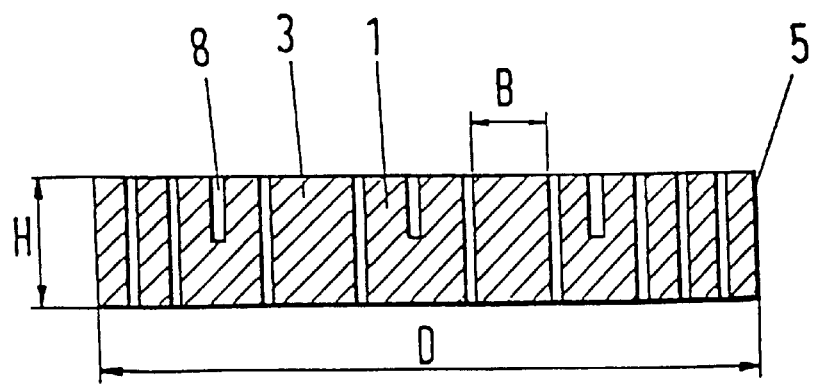
FIG. 2 is a cross-section through the spiral of FIG. 1.

The thickness of the elastic body which forms the spiral can however also decrease steadily from the inside outwards, so that no specially executed transition region is required. In FIG. 2 the spiral is shown in cross-section. It has a diameter in the range of 20 to 30 mm, preferably in the range from 23 to 25.5 mm. The height preferably amounts to 5–10 mm. The height can also increase continually in the direction of the center and take on a maximum of 10 mm at the center. The height can also be adapted to the individual curvature of the vertebral surfaces, which can be of especially of interest in the case of vertebral deformations.

A band-like stiffening 7 is fixed to the free end of the spiral 6 and projects beyond the free end so as to serve as an extension when handling the spiral. The transition should be as smooth as possible. The band should be capable of transmitting its shear forces and is preferably made of titanium for reasons of biocompatibility and sterilization. It is practical for its length to extend to approximately 20 cm, and it enables a guidance of the separation instrument up to the point of severance on the spiral.

The elastic body consists preferably of a plastic such as polyurethane with the spiral turns coming to lie form-fitted to the greatest extent in the absence of external forces. The elastic properties of the material must be such that the spiral form is again assumed even after it has been unrolled. The deformation properties of the material should be as similar to those of the intervertebral disc as possible and lie advantageously in the range of Shore hardness from about 70A to 90A, preferably around 80A.

The elastic body can be manufactured by being cut out of the material, which is possible in particular with the use of computer-guided lasers. Cutting processes which do not stress the material thermally are preferable, since this avoids toxic by-products and has no influence on the elastic properties of the material. It needs no special mention that the material itself should be sterilization.

In order to check on the position of the implant intra-operatively and post-operatively it is recommended to provide X-ray-positive markers in the form of points 8 or of a thread, which is not shown, on or along and within the elastic body. Barium, tantalum or the like can be used as the marker material.

The apparatus for inserting the elastic body is shown in more detail in FIG. 3. It comprises a rectangular tube 10 for receiving the spiral which is rolled up at least so far that its still protruding portion S can be inserted through the operatively created opening into the intervertebral region without problem. The hollow tube 10 preferably has a one-sided cross-section narrowing 11 at the distal end which is formed in the shape of a cone or a beak. The tube can also have a curvature, which eases the access to the intervertebral region from the side dorsally and is selected to match the hand preference of the user. The curvature can also be directed caudally or cranially depending on the requirements.

The feeding of the body can also be done by hand. Gripping means to support the tube are helpful for this purpose. They can be formed coaxial with the tube in the form of a thickened portion or can extend radially to the tube axis. Preferably, however, feed means are provided in the form of an elastic pusher tool 12, which can for example, be operated via a lever mechanism 13. At its distal end, and standing in effective connection with the elastic body or with the stiffening, the pusher tool has means 14 which facilitate the feeding of the body. The means can consist of a roughening of the surface or alternatively in tooth-like extensions with preferential orientation in the distal direction. By this means it can be achieved that when the pusher tool is pushed forward, the extensions engage the elastic body or the stiffening and push it along, whereas they glide over the surface when the pusher tool is retracted, making possible a controlled feeding of the elastic body. The one-sided cross-sectional narrowing 11 of the rectangular tube 10 causes the pusher tool to be pressed downwards at the same time as it is being pushed forwards, and thus strengthens the grip between the pusher tool and the body. Due to the fact that the pusher tool grips the unrolled spiral very far forward, the latter is practically drawn through the hollow tube, so that it does not block itself due to its own stress, as could easily be the case when the thrust is from the rear.

FIGS. 4 and 5 show an apparatus for severing off the superfluous end of the spiral. After the intervertebral prosthesis has been implanted the insertion apparatus is drawn back along the stiffening 7, which remains outside the intervertebral region, and the separation instrument 20 pushed onto it. This instrument preferably has an action mechanism similar to a pair of pliers, comprising two grip parts 21, 22 which are connected to one another via a hinge 23. One jaw 24 is provided with a recess 25 in the longitudinal direction into which the stiffening 7 and/or the elastic body 5, 6 can be taken up. The other jaw 26 has a cutting edge 27 which is movable essentially transversely to the recess 25. The length of the jaws as well as the placement of the cutting edge in the distal direction is preferably chosen in such a manner that, on the one hand, a cut within the intervertebral region is possible and, on the other hand, that the required separation forces can be applied safely. The cutting blade itself can be executed as a replaceable blade. Of course pliers whose grip parts meet the longitudinal axis at an angle can also be used in accordance with the invention.

After the elastic body is shortened to the desired length the severing apparatus is drawnback along with the stiffening 7. The implant takes on the spiral form due to its form-stable properties. The implant retains its spiral form even under load without a special fastening of the free end being necessary.

The previously described process for inserting a spiral implant into a cavity can also be advantageously used for purposes of teaching, practice or demonstration.

What is claimed is:

1. A method for inserting a spiral intervertebral prosthesis into a cavity of an intervertebral disc, the prosthesis having an elongated, elastic body, which is form-elastic and which rolls up by itself into the form of at least one plane spiral in the force-free state, the method comprising the following steps:

taking up at least a portion of the elastic body of the prosthesis, which is rolled up into a spiral in the force-free state, into a hollow space of an insertion apparatus provided for this purpose, introducing the elastic body through an opening of the cavity by means of the insertion apparatus, metering advance of the spiral body out of the insertion apparatus, with the body rolling up by itself in a plane spiral form within the cavity, withdrawing the insertion apparatus along a second portion of straightened spiral remaining outside the cavity, applying a severing apparatus along the second portion and severing the elastic body at the desired place, and removing the severing apparatus and the severed-off portion.

* * * * *